United States Patent [19]

Dhabhar et al.

[11] Patent Number: 4,474,902

[45] Date of Patent: Oct. 2, 1984

[54] KARAYA GUM ADHESIVE IN A HYDROPHILIC DENTURE VEHICLE

[75] Inventors: Dadi J. Dhabhar, Norwalk; Nicholas F. Schmidt, Brookfield, both of Conn.

[73] Assignee: Richardson-Vicks Inc., Wilton, Conn.

[21] Appl. No.: 447,481

[22] Filed: Dec. 7, 1982

[51] Int. Cl.³ .................. A61K 6/00; C08L 1/32; C09K 3/00
[52] U.S. Cl. ...................... 523/120; 106/35; 524/27; 524/45
[58] Field of Search .............. 106/35, 205–209; 523/120; 424/361–363, 34; 524/27, 45; 433/168, 172, 180

[56] References Cited

U.S. PATENT DOCUMENTS

| | | | |
|---|---|---|---|
| 2,978,812 | 4/1961 | Rosenthal et al. | 528/421 |
| 3,102,838 | 9/1963 | Hervey | 162/152 |
| 3,868,259 | 2/1975 | Keegan et al. | 106/35 |
| 4,198,243 | 4/1980 | Tanaka | 106/35 |
| 4,373,036 | 2/1983 | Chang et al. | 523/120 |

FOREIGN PATENT DOCUMENTS 8131 2/1980 European Pat. Off. .............. 106/35

Primary Examiner—Theodore Morris
Attorney, Agent, or Firm—Salvatore R. Conte

[57] ABSTRACT

An improved denture adhesive containing a karaya gum adhesive component in a hydrophilic vehicle comprising certain polyethylene glycols and, as an optional component in certain forms of the subject adhesives, glycerin, for enhancing pharmaceutical elegance of the final product.

25 Claims, No Drawings

KARAYA GUM ADHESIVE IN A HYDROPHILIC DENTURE VEHICLE

SUMMARY OF THE INVENTION

A highly effective hydrophilic denture adhesive composition is provided comprising a substantially anhydrous mixture of, as one essential component, an effective adhesive amount of a karaya gum fraction consisting essentially of karaya gum or karaya gum in combination with sodium carboxymethylcellulose and/or ethylene oxide homopolymer, and, as another essential component, a hydrophilic vehicle comprising a polyethylene glycol (PEG) fraction with average viscosity of from about 44 to about 25,600 centipoises at about 60° C. Various forms of the subject compositions are available, for example, liquids, creams and powders. Optionally, up to about one-half of the polyethylene glycol fraction may be substituted with glycerin in the non-powder forms of the subject compositions. The denture adhesive composition may also have present colorants, flavoring agents, odorants, sweeteners and other additives in amounts generally employed for their respective intended purposes.

BACKGROUND OF THE INVENTION

Denture adhesive cream formulations have heretofore been comprised mainly of natural or synthetic polymeric adhesives suspended in an anhydrous oleagenous vehicle system generally consisting of mineral oil and/or petrolatum. These hydrophobic formulations have viscosities ranging from moderately thick to very thick making them difficult to squeeze out evenly and fluidly from the generally employed collapsible tubes or containers. However, this thickness range is necessary to prevent syneresis (i.e., phase separation) from occurring due to the solid adhesive particles being only suspended in the hydrophobic vehicle.

More recently, liquid denture adhesives have been reported containing sodium carboxymethylcellulose and ethylene oxide homopolymer as the solid adhesives suspended in mineral oil (e.g. see U.S. patent application Ser. No. 140,462). Examples of such hydrophobic denture adhesives are the products commercially available from Block Drug Company, Inc. in the United States under the trademark "Dentrol" and in West Germany under the trademark "Cedenta", which are believed to contain about 41-45% w/w of sodium carboxymethylcellulose and ethylene oxide homopolymer in a mineral oil base. However, upon standing, considerable phase separation occurs thus requiring a "shake well" indication on the container.

Furthermore, whereas such formulations may be effective in securing dentures quickly within the oral cavity, it may be necessary to apply more than one application per day to obtain sufficient adhesion throughout the day, depending on the fit of the denture and the psychological need of the denture wearer. Such multiple applications are inconvenient and at times impractical or impossible and, therefore, these heretofore known denture adhesive liquids are not totally acceptable and in some cases undesirable.

Whereas these conventional types of denture adhesive creams and liquids have provided good stabilizing-/hold properties to denture wearers, some organoleptic negatives have also been perceived with these products. Some of these commonly perceived negatives are, for example, unpleasant mouth feel, bad taste, grittiness, oily sensation in the mouth and difficulty of application and removal from dentures. Another disadvantage is that the salivary fluids have to penetrate a hydrophobic vehicle in order to reach and hydrate the adhesive system. This hydrophobic barrier may cause a time lag before the adhesive is hydrated and starts to work. Due to such slowed rate of hydration of adhesive components, there results a lack of immediate denture hold.

It has therefore been desirable to provide a denture adhesive of superior adherent properties over prolonged periods of time. Such is accomplished with the denture adhesive compositions herein described, a unique combination of an adhesive gum system in a hydrophilic vehicle system which eliminates many of the aforementioned disadvantages found with denture adhesives having conventional oleagenous vehicle systems. For example, the hydrophilicity of this unique combination facilitates the penetration of the saliva to the adhesive gum system, thereby allowing quicker hydration, and, therefore, quicker hold. Test results hereinafter demonstrate the stronger hold of the subject compositions. Furthermore, they are available in forms with variable consistencies, for example, liquids, creams and powders.

In our copending application Ser. No. 361,631, filed Mar. 26, 1982, entitled "Hydrophilic Denture Adhesive", the use of a polymeric adhesive system comprising sodium carboxymethylcellulose in admixture with an ethylene oxide homopolymer in specified ratios together with a hydrophilic PEG vehicle was described. In contrast, the instant compositions utilize karaya gum alone or with said sodium carboxymethylcellulose and/or said ethylene oxide homopolymer as the adhesive component in the hydrophilic PEG vehicle.

DETAILED DESCRIPTION OF THE INVENTION

This invention relates to a hydrophilic denture adhesive composition which, when in contact with saliva, hydrates within the oral cavity to provide superior adherent properties. The composition comprises two essential components. The first is an adhesive fraction consisting essentially of karaya gum alone or in combination with either or both of sodium carboxymethylcellulose and ethylene oxide homopolymer. The second is a hydrophilic vehicle comprising a polyethylene glycol fraction with average viscosity of from about 44 to about 25,600 centipoises when measured at about 60° C., generally 60°±2° C.

With regard to the adhesive component, the karaya gum, sodium carboxymethylcellulose and ethylene oxide homopolymer constituents are well known and commercially available.

Karaya gum is an adherent natural gum, readily available as a fine powder and used heretofore to secure dentures. It has the ability to swell many times its original volume upon the addition of water to form a gelatinous or mucilaginous mass.

Sodium carboxymethylcellulose is also a powder which, when moistened, becomes hydrated and tacky or gummy in consistency with adhesive characteristics. The sodium carboxymethylcellulose "gums" employed in this invention are water soluble, anoinic, long chain polymers, derived from cellulose. Properties vary with the average number of carboxy methyl groups that are substituted per anhydroglucose unit in each cellulose molecule. This property is generally referred to as "the degree of substitution", with the maximum substitution possible designated as "3.0" since there are just three hydroxy groups capable of reaction in each anhydroglucose unit. For the practice of this invention, it has been found that one or more such cellulose gums having a degree of substitution of from about 0.4 to about 1.2 is suitable. The viscosity of a 1 percent solution of the gum, measured at 25° C., should be in the range of from about 400 to 4,500, preferably 1,500 to 2,500 centipoises.

Sodium carboxymethylcellulose gums of this type are more fully described in "Chemical and Physical Properties: Cellulose Gum," 1978, published by Hercules, Incorporated, Coatings and Specialty Products Department, 910 Market Street, Wilmington, Del. 19899.

As examples of commercially available sodium carboxymethylcellulose gums suitable for use in this invention there may be mentioned those sold by Hercules, Incorporated, Wilmington, Del., as types 4H1, 7H, 9H4, 7H3S, 7H0F and 7H4. Type 7H3S is preferred for use in this invention.

The ethylene oxide hompolymers employed in the compositions of the invention are water soluble nonionic poly(ethylene oxide) homopolymers having molecular weights of from about 100,000 to about 5,000,000. The polymers have the structure $+O-CH_2CH_2+_n$ wherein n represents the degree of polymerization and has a value of from about 2,000 to about 100,000. These polymers are white powders. When moistened, they become hydrated and tacky or gummy in consistency with adhesive characteristics.

Poly(ethylene oxide) homopolymers of this type are more fully described in "Polyox", 1978, published by Union Carbide Corporation, 270 Park Avenue, New York, N.Y. 10017, as Technical Bulletin F-44029B.

As examples of commercially available powdered poly(ethylene oxide) homopolymers suitable for use in this invention there may be mentioned those polymers sold by Union Carbide Corporation under the trademark POLYOX as grades WSR N-10, WSR N-80, WSR N-750, WSR N-3000, WSR-205, WSR-1105 and WSR-301. Preferred for use in this invention is POLYOX WSR-301 homopolymer.

In the compositions of this invention the adhesive component may be solely karaya gum or a combination of karaya gum with either of sodium carboxymethylcellulose or poly(ethylene oxide) homopolymer or both. With karaya gum as the sole adherent, the subject compositions comprise from about 35 to about 55 percent by weight of karaya gum, based on the total weight of the composition (i.e., "% w/w"), and from about 45 to about 65% w/w of the polyethylene glycol (PEG) fraction.

When the karaya gum is used in admixture with sodium carboxymethylcellulose to form the adhesive component, the subject compositions comprise from about 25 to about 50% w/w of such adhesive component and from about 50 to about 75% w/w of the PEG fraction. When the karaya gum is used is admixture with poly(ethylene oxide) homopolymer to form the adhesive component, the subject compositions comprise from about 25 to about 40% w/w of such adhesive component and from about 60 to about 75% w/w of the PEG fraction. In addition, the weight ratio of karaya gum to either of the sodium carboxymethylcellulose or the poly(ethylene oxide) homopolymer, when combined to form a two-ingredient adhesive component, preferably ranges from about 4:1 to about 1:4, respectively.

When the karaya gum, sodium carboxymethylcellulose and poly(ethylene oxide) homopolymer are combined to form a three-ingredient adhesive component, the subject compositions comprise from about 25 to about 50% w/w of such adhesive component and from about 50 to about 75% w/w of the PEG fraction, and the respective weight ratio of the three ingredients is perferably about 1:1:1.

With regard to the hydrophilic vehicle component, the polyethylene glycols suitable for use in the compositions of the invention are also well known and commercially available, for example, those marketed by Union Carbide Corporation under its trademark "Carbowax".

Polyethylene glycols are polymers of ethylene oxide with the generalized formula $HOCH_2(CH_2OCH_2)_n-CH_2OH$ wherein n represents the average number of oxyethylene groups. These polyethylene glycols, which are designated by a number that represents the average molecular weight, range from clear viscous liquids at room temperature (e.g., PEGs 200, 300, 400 and 600) to soft solids (e.g. PEGS 1000 and 1450) to waxy solids available in the form of flakes or powders (e.g. PEGs 3350 and 8000) to granular solids (e.g., PEG 14,000). All these polymers dissolve in water to form clear solutions and this water solubility feature imparts a hydrophilic characteristic to the compositions of this invention.

The polyethylene glycol (PEG) fraction, comprising one or more polyethylene glycols each having an average molecular weight of from about 200 to about 20,000, of the subject compositions have an average viscosity when measured at about 60° C. of from about 44 to about 25,600 centipoises (cps), preferably from about 44 to about 2,500 cps, and most preferably from about 44 to about 300 cps, as determined, for example, by an instrument such as the Brookfield RVT Viscometer. Either individual polyethylene glycols or blends of two or more polyethylene glycols within this viscosity range may be utilized. For example, and without being limited thereto, a blend of liquid PEG 400 or PEG 600 and solid PEG 8000 in a respective weight ratio of from about 9:1 to about 33:1, has been found particularly suitable for the lotion-like liquids and soft creams of this invention.

The data presented in following Table 1 illustrate the variety of final product consistencies obtainable according to this invention by varying the make-up of the PEG fraction in a particular formulation. In Example 3 hereafter, a lotion liquid formulation is described which contains 33% w/w adhesives, 10% w/w glycerin and 57% PEGs, the latter made up of PEG 400 and PEG 8000 in a ratio of about 24:1, respectively. By substituting an equivalent amount of total PEG but in the indicated varying ratios, the following results are approximated:

TABLE 1

| Vehicle Ratio (PEG 400: PEG 8000) | PEG Fraction Viscosity** (cps @ 60° C.) | Product Consistency |
|---|---|---|
| 100:0 | 56 | liquid |
| 98:2 (49:1) | 44 | liquid |
| 97:3 (32.3:1) | 61 | liquid lotion |
| 94:6 (19:1) | 72 | liquid lotion |
| 92:8 (11.5:1) | 94 | liquid lotion |
| 90:10 (9:1) | 94 | soft cream |
| 80:20 (4:1) | 170 | cream |
| 70:30 (2.3:1) | 315 | thick cream |
| 60:40 (1.5:1) | 600 | very thick cream |
| 0:100 (PEG 8000*) | 2,500 | powder |

TABLE 1-continued

| Vehicle Ratio (PEG 400: PEG 8000) | PEG Fraction Viscosity** (cps @ 60° C.) | Product Consistency |
|---|---|---|
| 0:100 (PEG 14000*) | 25,600 | powder |

*The 10% w/w glycerin replaced by an equal amount of PEG.
**Determined on a Brookfield RVT Viscometer.

By blending members of the PEG series, different viscosities within the defined range may be obtained, as desired. For example, by utilizing increasing amounts of higher molecular weight PEGs, i.e. more solids than liquids, the resultant viscosity of the polyethylene glycol fraction will also increase (assuming other ingredients in the denture adhesive composition are maintained constant) so that one can readily obtain embodiments of the subject compositions ranging in consistency from viscous liquids to creams and powders. For example, with about 32 percent w/w of the adhesive fraction and 10 percent w/w of glycerin, a polyethylene glycol fraction having a viscosity at about 60° C. of about 44–95 cps affords a final product with a liquid lotion to soft cream consistency; whereas a polyethylene glycol fraction having a viscosity of about 100–300 cps affords a cream type of final product; whereas a polyethylene glycol fraction above 300 cps affords a thick creamy product; and whereas without glycerin a polyethylene glycol fraction having a very high viscosity of about 2500–25,600 cps affords a final product in powder form. This ability to adjust the fluidity of the final product is a particularly advantageous feature of the invention since it affords commercialization of final product forms with consumer acceptable consistencies such as (i) liquids and soft creams, which are readily extrudable from appropriate containers, for example, pump action bottles, squeezable tubes and the like, (ii) thicker creams and (iii) powders, all of which forms are suitable for easy application to dentures.

With regard to the liquid and cream compositions of this invention, one particular ingredient that is preferred and recommended as a substitute for part of the polyethylene glycol fraction is glycerin which has a known soothing effect on oral gum tissue and also affords a pleasant mouth feel and sweetening taste to the finished composition. Due to its humectant character, glycerin also contributes to the hydrophilicity of the finished composition, thereby allowing quicker hydration on contact with moisture or saliva. Thus, although glycerin is not an essential component of the hydrophilic vehicle or of the finished composition, it does enhance the latter's esthetic appearance and acceptability.

It has been found that a significant amount of glycerin can be substituted for the polyethylene glycol fraction, for example, up to about one-half of the latter may be so substituted without any significant detriment to the overall adhesive ability of the finished composition. However, due to the increased cost incurred with high amounts of the relatively expensive glycerin, about 25% w/w of glycerin is recommended as the upper limit with about 5 to about 15 percent w/w being preferred and about 10 percent w/w most preferred.

Any suitable flavoring agent, colorant, odorant, natural or synthetic sweetener, deodorant, antimicrobial agent, tissue healing agent or other optional ingredient generally employed as an additive in denture adhesives may be utilized in the compositions of this invention, if so desired, so long as such addition is not detrimental to the overall adhesive ability of the compositions. Preferably, up to about 1.0% w/w of such additives may be utilized.

Typical of the compositions encompassed in the present invention are the formulations exemplified in Table 2. the symbol "% w/w" indicates the weight of each ingredient based on the total weight of the particular composition.

TABLE 2

| | Formulation Examples in % w/w | | |
|---|---|---|---|
| | Ex. 1 | Ex. 2 | Ex. 3 |
| Karaya gum | 40.0 | 12.0 | 11.0 |
| Na—CMC[1] | | 14.0 | 11.0 |
| Polyox[2] | | 15.0 | 11.0 |
| PEG 400 | 44.0 | | 54.7 |
| PEG 600 | | | |
| PEG 8000 | 5.59 | 59.0 | 2.3 |
| Glycerin | 10.0 | | 10.0 |
| Colorant | 0.01 | | |
| Flavor[3] | 0.4 | | |
| | 100.00 | 100.0 | 100.0 |
| Form: | soft cream | powder | lotion |

[1]Sodium carboxymethylcellulose type 7H3S.
[2]Poly(ethylene oxide) homopolymer type WSR-301.
[3]Premix of mint oils.

The compositions of this invention can be produced by standard compounding techniques. For example, the liquid and cream compositions are readily prepared by heating with stirring the polyethylene glycol fraction to about 65°–70° C. at which temperature any solid or samisolid polyethylene glycols which may be present are liquified and the fraction has a syrupy gel-like consistency. The adhesive component, either karaya gym alone or in admixture with sodium carboxymethylcellulose and/or poly(ethylene oxide) homopolymer, is added to the polyethylene glycol fraction, slightly cooled to about 50°–60° C., with constant stirring to obtain a uniform adhesive/vehicle mixture. Any optional additives such as flavor, color and the like may then be incorporated into the adhesive/vehicle mixture. It is recommended, however, that the adhesive/vehicle mixture be cooled to about or slightly below 40° C. before incorporation of any such additives of a volatile character, for example, aromatic flavors, in order to preserve their characteristic essences.

When glycerin is to be included in the final product, it is advantageously added to and mixed into the slightly cooled (about 50°–60° C.) polyethylene glycol fraction prior to admixture with the adhesive component. The glycerin addition step may also be utilized as a way of carrying any compatible optional additive such as a sweetener, colorant and the like into the final product by simply mixing or dissolving the desired additive in the glycerin beforehand.

The powder compositions of this invention are readily obtained by simple admixture of the powder constituents of the adhesive component with the powder PEG fraction of the hydrophilic vehicle component. The preferred polyethylene glycol for making the powder compositions is PEG 8000 alone. It is recommended that granular forms of polyethylene glycol, such as PEG 14,000, be pulverized to a fine powder prior to admixture with the powder adhesive constituent(s).

The denture adhesive compositions of this invention possess superior and unexpected adhesion/cohesion properties as measured by the Texturometer evaluation test. The term Texturometer is a trademark for an instrument manufactured and sold by C. W. Brabender Instruments, Inc. of Hackensack, N.J. which enables a quantitative measurement of textural parameters of products. The instrument mechanically simulates the chewing motions of the human jaws. A plunger is driven through the test sample (approx. 3 ml) held in a sample holder under which there is a strain-gauge hooked up to a high-speed chart recorder. The instrument draws force-time curves which are indicative of the cohesive/adhesive ability of the test sample. The plunger is driven through the test sample at the rate of 12 times per minute and the chart paper speed is 1500 mm per minute.

The test sample is prepared by uniformly mixing the product to be tested with distilled water in a small mortar and pestle at a ratio of one part by weight of product to four parts by weight of water. The areas under the cohesion and adhesion parts of the force-time curves are measured and these areas are a measure of the cohesive/adhesive abilities of the hydrated adhesive formulation, i.e., the larger the areas, the greater such abilities. After the initial measurement, the test sample is kept undisturbed in a tightly covered petri-dish (to prevent evaporation) for 5 hours at 25° C. and then retested. Accordingly, in Table 3 hereafter, the tabulated numbers indicating the observed Texturometric evaluations represent areas under the cohesion/adhesion Texturometric curves. The unexpected superiority of the compositions of the present invention is demonstrated by the Texturometer evaluation data set forth in Table 3 wherein the compositions of Examples 4 through 19 are tested and compared with Example 20, a commercial product available under the brand name "Dentrol" from the Block Drug Company, Inc. This product, which does not contain karaya gum, has a mixture of sodium carboxymethylcellulose and ethylene oxide homopolymer as the adhesive constituents in a hydrophobic mineral oil vehicle rather than the hydrophilic PEG vehicle of this invention. The adhesive/cohesive properties of the tested hydrated products are evaluated initially and again after 5 hours.

TABLE 3

| Ex. No. | Test Prod.[2] | % w/w[3] | Weight Ratio | COHESION (sq. mm.) Initial | COHESION (sq. mm.) After 5 hrs. | ADHESION (sq. mm.) Initial | ADHESION (sq. mm.) After 5 hrs. |
|---|---|---|---|---|---|---|---|
| 4 | Karaya Gum | 55 | — | 454 | 454 | 254 | 241 |
| 5 | Karaya Gum | 50 | — | 414 | 334 | 281 | 160 |
| 6 | Karaya Gum | 35 | — | 234 | 241 | 156 | 160 |
| 7 | Karaya Gum + Na—CMC | 50 | 4:1 | 481 | 401 | 267 | 214 |
| 8 | Karaya Gum + Na—CMC | 25 | 4:1 | 134 | 74 | 94 | 40 |
| 9 | Karaya Gum + Na—CMC | 50 | 1:4 | 815 | 1430 | 241 | 241 |
| 10 | Karaya Gum + Na—CMC | 25 | 1:4 | 321 | 414 | 134 | 134 |
| 11 | Karaya Gum + Polyox | 50 | 4:1 | 815 | 695 | 334 | 401 |
| 12 | Karaya Gum + Polyox | 25 | 4:1 | 160 | 227 | 120 | 100 |
| 13 | Karaya Gum + Polyox | 35 | 1:4 | 254 | 838 | 241 | 606 |
| 14 | Karaya Gum + Polyox | 25 | 1:3 | 254 | 294 | 167 | 120 |
| 15 | Karaya Gum + Polyox | 40 | 1:3 | 381 | 722 | 167 | 495 |
| 16 | Karaya Gum + Polyox | 25 | 1:2 | 408 | 388 | 257 | 361 |
| 17 | Karaya Gum + Polyox | 40 | 1:2 | 301 | 779 | 190 | 401 |
| 18 | Karaya Gum + Polyox | 50 | 1:1:1 | 615 | 1094 | 374 | 1017 |
| 19 | Karaya Gum + Na—CMC + Polyox | 25 | 1:1:1 | 247 | 328 | 167 | 267 |
| 20 | Dentrol | — | — | 279 | 568 | 71 | 37 |

[1] Numbers represent areas under cohesion/adhesion Texturometric curves.
[2] "Na—CMC and "Polyox" same as in Table 2.
[3] Balance of composition is PEG 600.

The data listed in Table 3 shows clearly the unexpected and superior nature of the cohesion and adhesion parameters obtained with compositions of this invention. Particularly noteworthy is the general increase in both cohesion and adhesion abilities of the subject compositions after 5 hours. In contrast, the measured adhesion of the comparative commercial product decreased significantly, almost 50% after 5 hours. The marked cohesion and adhesion parameters after keeping for 5 hours, characteristic of the subject compositions, is even more surprising since it might be expected that with passing of time the water of hydration, considering the hydrophilicity of the subject compositions, might weaken rather than strengthen the structure of such compositions.

The foregoing in-vitro Texturometric evaluation data illustrate the effectiveness of the denture adhesive compositions of this invention. When in contact with moistened denture plates, gums and saliva, the subject compositions hydrate within the oral cavity to provide superior denture stabilizing properties not possessed by denture adhesives generally having hydrophobic vehicles for the adhesive components rather than hydrophilic vehicles as with the subject compositions.

We claim:

1. A denture adhesive composition comprising a substantially anhydrous mixture of:
   (a) an effective adhesive amount of a karaya gum fraction consisting essentially of karaya gum solely or in combination with either or both of sodium carboxymethylcellulose and poly(ethylene oxide) homopolymer; and
   (b) a polyethylene glycol fraction comprising one or more polyethylene glycols each having an average molecular weight of from about 200 to about 20,000 and said fraction having an average viscosity of from about 44 to about 25,600 centipoises at about 60° C.

2. The composition of claim 1 wherein (a) is an effective adhesive amount of karaya gum.

3. The composition of claim 1 wherein (a) is an effective adhesive amount of karaya gum in combination with sodium carboxymethylcellulose.

4. The composition of claim 1 wherein (a) is an effective adhesive amount of karaya gum in combination with poly(ethylene oxide) homopolymer.

5. The composition of claim 1 wherein (a) is an effective adhesive amount of karaya gum in combination with sodium carboxymethylcellulose and poly(ethylene oxide) homopolymer.

6. A denture adhesive composition comprising a substantially anhydrous mixture of:
 (a) from about 35 to about 55 percent w/w of karaya gum; and
 (b) from about 45 to about 65 percent w/w of a polyethylene glycol fraction comprising one or more polyethylene glycols each having a molecular weight of from about 200 to about 20,000 and said fraction having an average viscosity of from about 44 to about 2500 centipoises at about 60° C.

7. The composition of claim 6 wherein up to about one-half of said polyethylene glycol fraction is substituted with glycerin.

8. A denture adhesive composition comprising a substantially anhydrous mixture of:
 (a) from about 25 to about 50 percent w/w of karaya gum and sodium carboxymethylcellulose in a respective weight ratio of from about 4:1 to about 1:4; and
 (b) from about 50 to about 75 percent w/w of a polyethylene glycol fraction comprising one or more polyethylene glycols each having a molecular weight of from about 200 to about 20,000 and said fraction having an average viscosity of from about 44 to about 2500 centipoises at about 60° C.

9. The composition of claim 8 wherein up to about one-half of said polyethylene glycol fraction is substituted with glycerin.

10. A denture adhesive composition comprising a substantially anhydrous mixture of:
 (a) from about 25 to about 40 percent w/w of karaya gum and poly(ethylene oxide) homopolymer in a respective weight ratio of from about 4:1 to about 1:4; and
 (b) from about 60 to about 75 percent w/w of a polyethylene glycol fraction comprising one or more polyethylene glycols each having a molecular weight of from about 200 to about 20,000 and said fraction having an average viscosity of from about 44 to about 2500 centipoises at about 60° C.

11. The composition of claim 10 wherein up to about one-half of said polyethylene glycol fraction is substituted with glycerin.

12. A denture adhesive composition comprising a substantially anhydrous mixture of:
 (a) from about 25 to about 50 percent w/w of karaya gum, sodium carboxymethylcellulose and poly(ethylene oxide) homopolymer in a respective weight ratio of about 1:1:1; and
 (b) from about 50 to about 75 percent w/w of a polyethylene glycol fraction comprising one or more polyethylene glycols each having a molecular weight of from about 200 to about 20,000 and said fraction having an average viscosity of from about 44 to about 2500 centipoises at about 60° C.

13. The composition of claim 12 wherein up to about one-half of said polyethylene glycol fraction is substituted with glycerin.

14. A denture adhesive composition comprising a substantially anhydrous mixture of:
 (a) from about 35 to about 55 percent w/w of karaya gum;
 (b) up to about 25 percent w/w of glycerin; and
 (c) substantially the remainder of a polyethylene glycol fraction comprising one or more polyethylene glycols each having a molecular weight of from about 200 to about 20,000 and said fraction having an average viscosity of from about 44 to about 300 centipoises at about 60° C.

15. The composition of claim 14 wherein (b) comprises from about 5 to about 15 percent w/w of said glycerin.

16. The composition of claim 14 wherein (b) comprises about 10 percent w/w of said glycerin.

17. A denture adhesive composition comprising a substantially anhydrous mixture of:
 (a) from about 25 to about 50 percent w/w of karaya gum and sodium carboxymethylcellulose in a respective weight ratio of from about 4:1 to about 1:4;
 (b) up to about 25 percent w/w of glycerin; and
 (c) substantially the remainder of a polyethylene glycol fraction comprising one or more polyethylene glycols each having a molecular weight of from about 200 to about 20,000 and said fraction having an average viscosity of from about 44 to about 300 centipoises at about 60° C.

18. The composition of claim 17 wherein (b) comprises about 5 to about 15 percent w/w of said glycerin.

19. The composition of claim 17 wherein (b) comprises about 10 percent w/w of said glycerin.

20. A denture adhesive composition comprising a substantially anhydrous mixture of:
 (a) from about 25 to about 40 percent w/w of karaya gum and poly(ethylene oxide) homopolymer in a respective weight ratio of from about 4:1 to about 1:4;
 (b) up to about 25 percent w/w of glycerin; and
 (c) substantially the remainder of a polyethylene glycol fraction comprising one or more polyethylene glycols each having a molecular weight of from about 200 to about 20,000 and said fraction having an average viscosity of from about 44 to about 300 centipoises at about 60° C.

21. The composition of claim 20 wherein (b) comprises about 5 to about 15 percent w/w of said glycerin.

22. The composition of claim 20 wherein (b) comprises about 10 percent w/w of said glycerin.

23. A denture adhesive composition comprising a substantially anhydrous mixture of:
 (a) from about 25 to about 50 percent w/w of karaya gum, sodium carboxymethylcellulose and poly(ethylene oxide) homopolymer in a respective weight ratio of about 1:1:1;
 (b) up to about 25 percent w/w of glycerin; and
 (c) substantially the remainder of a polyethylene glycol fraction comprising one or more polyethylene glycols each having a molecular weight of from about 200 to about 20,000 and said fraction having an average viscosity of from about 44 to about 300 centipoises at about 60° C.

24. The composition of claim 23 wherein (b) comprises about 5 to about 15 percent w/w of said glycerin.

25. The composition of claim 23 wherein (b) comprises about 10 percent w/w of said glycerin.

* * * * *